United States Patent [19]

Dirr, Jr. et al.

[11] Patent Number: 5,267,980

[45] Date of Patent: Dec. 7, 1993

[54] OPTICAL COMPONENTS FOR AN I.V. FLOW DETECTOR

[75] Inventors: William J. Dirr, Jr., Cincinnati; Thomas E. Kimble, Glendale, both of Ohio

[73] Assignee: Random Corporation, Cincinnati, Ohio

[21] Appl. No.: 575,401

[22] Filed: Aug. 29, 1990

[51] Int. Cl.$^5$ ............................................. A61M 5/00
[52] U.S. Cl. ............................. 604/253; 128/DIG. 13
[58] Field of Search ......................... 73/861.41, 861.05; 604/253, 251, 65–67; 250/574, 573, 576; 356/440, 442, 335, 336; 128/DIG. 12–13

[56] References Cited

U.S. PATENT DOCUMENTS

4,680,977 7/1987 Contero et al. ................. 73/861.41

Primary Examiner—C. Fred Rosenbaum
Assistant Examiner—Manuel Mendez
Attorney, Agent, or Firm—Eugene F. Friedman

[57] ABSTRACT

Optical components and methods for an I.V. flow detector providing complete coverage of a drip chamber through the use of a single emitter and receiver. The optical components take the light of a single emitter and spread it uniformly across the entire drip chamber. Furthermore, the light is collimated as it passes through the chamber. In addition, the optics collimates the light at some point in its path from the emitter to the drip chamber. Similarly, it collimates the beam of radiation at some point in its path from the drip chamber to the receiver. Further, the optics creates a plane of symmetry for the light path passing through the center of the drip chamber and lies perpendicular to the path of the light. The design specifically takes into account the optical characteristics of the drip chamber itself.

66 Claims, 3 Drawing Sheets

OPTICAL COMPONENTS FOR AN I.V. FLOW DETECTOR

REFERENCE TO RELATED APPLICATION

An I.V. flow detector making use of the optical components of the present application may also incorporate the circuit shown in U.S. patent application Ser. No. 07/575,400 of William J. Dirr, Jr. filed on Aug. 29, 1990.

BACKGROUND

Intravenous fluid delivery systems often incorporate a device for determining the actual flow of the liquid to the patient. The detector may operate by determining when each drop has fallen in a drip chamber.

To accomplish this objective, the system passes a beam of electromagnetic radiation through the drip chamber itself. The passage of a drop should, under varying conditions, interrupt the light beam which the detector may then discover. It utilizes this information to determine that a drop indeed has fallen.

The difficulty encountered by this type of flow detector centers upon the necessity of detecting a drop falling anywhere in the drip chamber itself. The use of a beam emanating from a single emitter and traveling to a single receiver has not provided coverage for the entire interior of the drip chamber with substantially uniform radiation. Thus, a drop passing along the side of the beam may not create a sufficient disturbance of the light path to result in the actual determination that a drop has fallen. The situation can occur particularly when the drip chamber hangs at an angle as when a patient may in effect pull on it when moving about in his bed. The problem becomes particularly difficult when the drip chamber hangs at such an angle that the drop, rather than falling, actually slides down the side of the chamber. Under these circumstances, drops will very likely escape the light beam and go totally undetected.

In an effort to avoid the nondetection of drops passing on the side of the beam of light, more recent flow detectors employ several beams of light from various emitters criss-crossing the drip chamber to separate detectors. This presumably provides more complete coverage of the drip chamber to avoid a drop escaping interrupting any one particular beam. However, a drop interrupting one light beam can very well give reflectances that detectors for other light beams may well receive. These various signals may result in the circuitry connecting to the receivers actually determining that no drop has fallen. Additionally, dead areas may exist between the various beams that would permit drops, especially flowing along the side, to again escape detection. Accordingly, the search continues for improved optical systems for flow detectors that will provide assurance that all drops will undergo detection.

SUMMARY

Utilizing various optical components will permit the utilization of the radiation from a single emitter traveling to a single receiver to cover the entire width of the interior of a drip chamber. Taking into account the optical characteristics of the drip chamber itself results in a system in which virtually all drops falling through the drip chamber (or flowing down its side) will interrupt the light beam passing through it in a manner that will result in its detection for an accurate determination of the fluid passing to the patient.

Typically, a drop detector includes an emitter means for providing electromagnetic radiation. Naturally, it also has a receiver means for, upon the receipt of such em. radiation, providing a characteristic electrical signal. A retaining device couples to the emitter means and the receiver means and holds a "transparent" drip chamber composed of the material having an index of refraction and a general shape; the drops of the I.V. liquid pass through the drip chamber. Lastly, optical means, coupled to the retaining means, alters the path of the em. radiation from the emitter means through a particular drip chamber held by the retaining means and to the receiver means.

An improved detector results when the optical means places the em. radiation from the emitter means, prior to its entry into the particular chamber, in a direction that will result in the beam of radiation being collimated when traveling in the interior of the chamber itself. It permits the coverage of the entire interior of the drip chamber by a beam of radiation substantially constant across the entire width of the chamber. A converging or diverging beam tends to leave "dead" areas where a drop could possibly hide and pass through undetected.

Alternately, the optical components, after the em. radiation has passed through the particular chamber, may collimate that radiation. This provides a path which allows for the collection of the radiation that has passed through the chamber possibly through a falling drop. It also permits the design of optical components between the emitter and the drip chamber and between the chamber and the receiver and allows for the complete coverage of the interior of the chamber as well as the collection of that radiation by the receiver. Accomplishing the collimation of the radiation after it passes through the drip chamber, as suggested above, involves treating the material of the drip chamber itself as an optical component. In fact, the design of the system commences with an analysis of the effect of the drip chamber itself, which generally has cyclindrical symmetry, upon the path of the light passing through it.

The design of an improved system becomes substantially facilitated where the path of the em. radiation displays bilateral symmetry on a plane passing through the center of the drip chamber. The plane should also lie perpendicular to the path of the radiation itself. This facilitates the use of radiation that covers the entire width of the interior of the drip chamber, generally in a collimated fashion, as well as identical optical components on the side of the drip chamber towards the emitter and on the other side towards the receiver.

Where the radiation passing through the drip chamber emanates from a first single location and the receiver obtains the radiation at a second single location, an improved detector results where the electromagnetic radiation entering the chamber has its beam expanded from the first location to a width at least about equal to the interior dimension of the chamber. After the radiation has existed the chamber, the beam having a width again at least about equal to the interior dimensions of said chamber condenses to the receiver. This results in the coverage of the entire interior of the chamber by the beam of radiation emanating from a single source. Furthermore, when the light covering the entire chamber then condenses to the single receiver, it avoids the possible interference caused by several emitters and receivers and helps eliminate dead areas that may very likely result otherwise.

A method of detecting drops falling through a drip chamber located in an area generally includes passing electromagnetic radiation through the chamber in that area. At least a portion of the electromagnetic radiation, after it has passed through the area, is received and its magnatude determined. An improved method involves placing the em. radiation, prior to its passage through the chamber, in a direction that would result in the radiation passing in a collimated fashion through the interior of the chamber. As a separate aspect, the radiation should undergo collimation, at some point, after it has passed through the chamber. For a further aspect, the radiation may have its path altered in a fashion that it becomes symmetrical about a plane passing through the center of the chamber and lying perpendicular to the path.

The method may also involve utilizing radiation through the chamber that emanates from a first single location and receiving such radiation at a second single location. In that instance, prior to the entry of the radiation into the chamber, its beam expands to a width at least about equal to the interior dimension of the chamber. After it exits the chamber, a beam of a width at least about equal to the interior dimension condenses to the second location where it is received. The coverage of the chamber thus provided will allow detection of a drop even when the chamber leans at an angle even up to 30 degrees from the vertical

DETAILED DESCRIPTION

Figure 1:
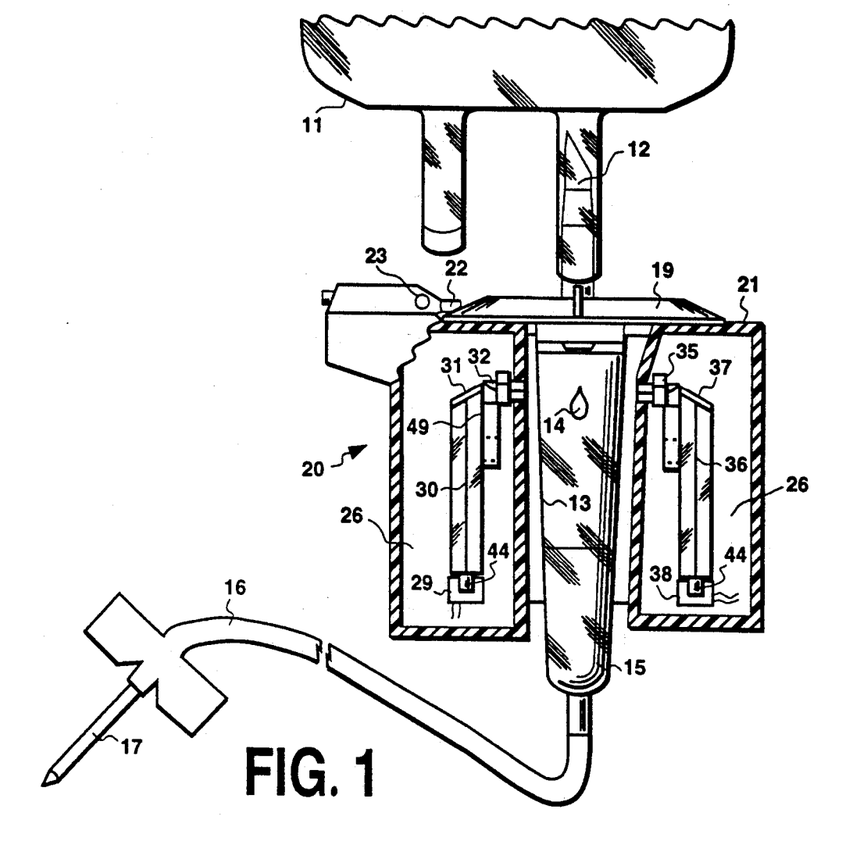
FIG. 1 shows, in partial section, a flow detector located about a drip chamber through which fluid passes from a source to a needle from which it can enter the patient.

As seen in FIG. 1, the intravenous solution flows from the bag or bottle 11 into the needle 12 of the I.V. set. From there it passes through the drip chamber 13 in the form of the drops 14 into the pool of liquid 15. It then travels through the tube 16 and out the needle 17 to the patient.

The plate 19 attaches to the drip chamber 13 and serves to keep it generally in place in the flow detector generally at 20. Specifically, the plate 19 sits on the top 21 of the detector 20. The spring-loaded pin 22, operating against the bias of the spring and locked in place, keeps the header 19 in its proper location. Pushing the button 23 releases the spring-loaded pin so that it may move to the left and free the drip chamber 15.

The optics for the flow detector sits within the housing 26 of the detector 20. Infrared radiation emanates from the emitter 29 which may take the form of a SE3470-3 LED. Infrared light then passes through the reflector 30. As the light hits the top 31 of the reflector 30, it bends 90 degrees through total internal reflectance. It then departs the relector 30 and passes through the lens 32 and across the entire drip chamber 15 into the receiver lens 35. From the receiver lens 32, it passes into the receiver reflector 36 undergoing total internal reflectance at the surface 37. It then travels downward into the receiver 38 which may take the form of a SFH317F phototransistor.

Figure 2:
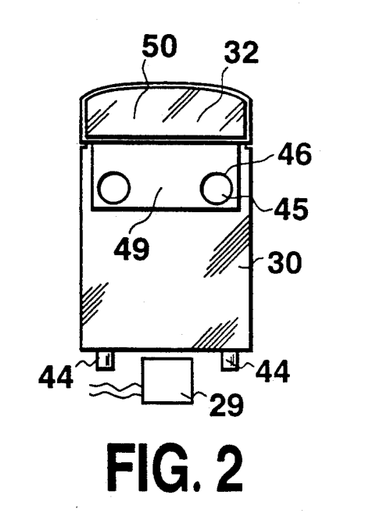
FIG. 2 shows the optics used in the drip chamber in FIG. 1 from the side facing the drip chamber.
Figure 3:
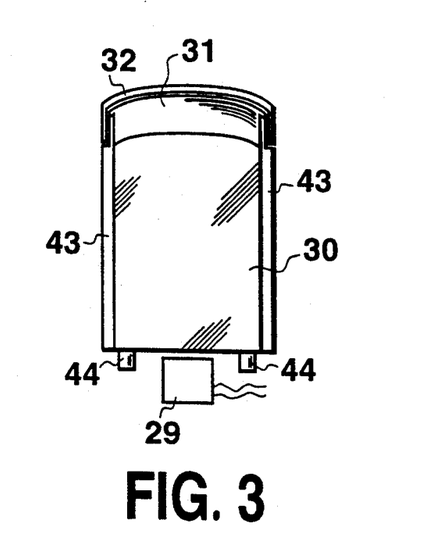
FIG. 3 shows the same optical components of FIG. 2 but from the side away from the drip chamber.
Figure 4:
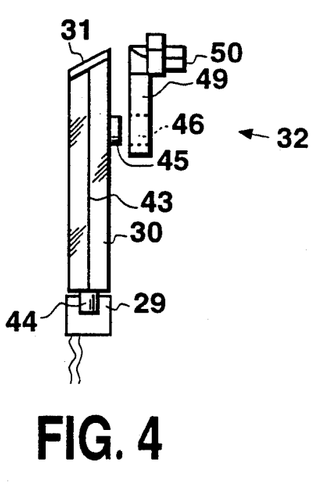
FIG. 4 provides a partially exploded view of the optical components seen in FIGS. 1 to 3.

The optical components appear more clearly in FIGS. 2, 3 and 4. These pictures show, specifically, the components of the emitter optics 29 to 32. However, with the exception of the substitution of the receiver 38 for the emitter 29, the receiver and emitter are optics completely identical. In fact, their manufacture involves making only one type of optics and simply turning them around and placing them on the different sides of the detector interior 26.

The figures show that the receiver 30 includes the ridge 43 which fits into grooves in the housing of the detector 20. This helps orient the various optical components. Additionally, the tabs 44 on the bottom of the reflectors 30 help locate it relative to the LED 29. Further, the protruding posts 45 fit into the opening 46 of the lens element 32 to help properly orient those two elements relative to each other. The lens base 49 holds the refracting portion 50 at its proper location.

Figure 5:
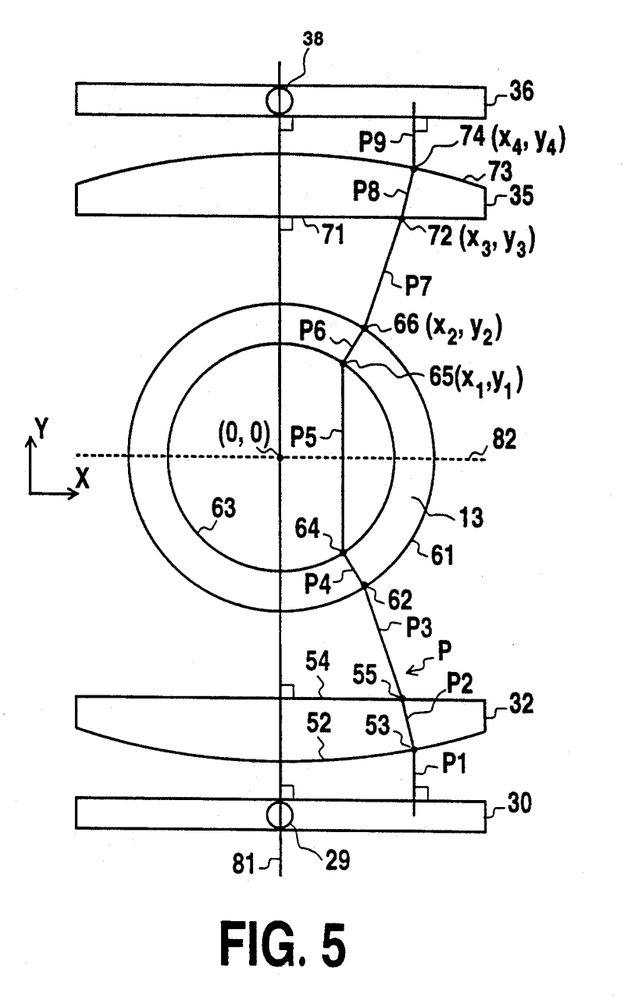
FIG. 5 illustrates diagramatically, from the top of the optical components in drip chamber FIG. 1, the path taken by radiation from the emitter through the various optical components, including the drip chamber, to the receiver.

FIG. 5 shows the path of the light as it travels through the various optical components 30 to 36 as well as the drip chamber 13. Referring to FIGS. 1 to 4 may also assist in understanding the diagram seen in FIG. 5. Initially, light from the emitter 29 travels upward (toward the reader as seen in FIG. 5) through the reflector 30. The emitter 29 generally provides a cone of radiation having a width of about 60 degrees. The radiation, when it hits the wall 31 (as seen in FIGS. 1, 3, and 4,) bends 90 degrees at the reflector 39 to form the initial portion P1 of its path as seen in FIG. 5. It then strikes the convex surface 52 of the lens 32, at the point 53 for example. The light undergoes refraction at the air-acrylic interface which occurs at the point 53. Subsequently, the light continues through the lens 32 along the path portion P2 until it reaches the flat surface 54 at the point 55. It undergoes further refraction at the acrylic-air interface which occurs at the surface 54.

The light continues to travel from the lens 32, along the path segment P3. The light subsequently contacts the outer surface 61 of the drip chamber 13 at the point 62. At the outer surface 61, it again undergoes refraction which it also experiences at the inner surface 63 at the point 64. The light now enters the interior of the drip chamber 13 along the path segment P5. There, drops falling through the chamber 13 should interrupt the light traveling along some path to provide an indication of the drop's having fallen through the chamber. The radiation, if it has not been interrupted by a falling drop, then restrikes the inner surface 63 of the drip chamber at the point 65 and, after traveling along the path segment P6, the outer surface 61 at the point 66. At both of the surfaces 61 and 63, the light again undergoes refraction.

After traveling along the path segment P7, the light strikes the flat surface 71 of the receptor lens 35 at the point 72, travels along the path segment P8 through the lens 35, and passes through the rear surface 73 of the lens 35 at the point 74. It then shines along the path segment P9 to reach the receiver reflector 36 which sends it to the detector 38.

The diagram shown and described in FIG. 5 in conjunction with the earlier figures merits a number of remarks. Initially, as clearly seen in FIG. 5, the optical components 30, 32, and 36, as well as the drip chamber 13 display bilateral symmetry about the midline 81 of the system. Thus taking the x-y axes as shown to the left of FIG. 5, the same equations and the same paths would result on the left side of the figure by substituting $-x$ for x. As a consequence, the midplane 85 makes right angles with the reflector surface 30, the flat surface 54 the lens 32, the flat surface 71 of the receiver lens 35, and the receiver reflector 36.

Secondly, as seen mostly clearly in FIG. 3, the reflector 31 describes a curved, as opposed to a flat, plane. Thus, as the radiation travels through the drip chamber 13, it does not have the appearance of a flat plane as a page itself might describe. Rather, the light might have more the appearance of the paper if the paper were bent in its middle up towards the reader as seen in FIG. 5. This curvature of the plane of light described by the light permits the facile reflection by the reflecting surfaces 31 and 37 to direct the light from the emitter 29 and to the receiver 38. Without the curvature, the light from the emitter would not, after passage from the reflector surface 31 pass in a collimated fashion from the reflector 30 to the lens 32. Rather, it would diverge away from the center plane 81. Similarly, at the other end, without the curvature, the light hitting the receiver reflector surface 37 would not focus at the detector 38. Thus, as a result, the light leaving the reflector 30 is collimated until it reaches the lens 32. This permits the reasonable calculation of the path for the light to take through the lens 32 and into the drip chamber 13 to achieve collimation in the interior of the chamber 13. Moreover, the assembly allows for the calculation of the lens 35 to achieve collimation along the path segment P9 into the receiver reflector 36. This in turn allows the condensing of the light striking the reflector surface 37 of the reflector 36 to the single detector 38.

Lastly, the construction of the system shown in FIG. 5 mandates bilateral symmetry about the midplane 82 shown in dashed lines in FIG. 5. This will permit calculation of one half of the path from either the emitter 81 to the longitudinal midplane 82 or from the midplane 82 to the detector 38. The other half results immediately from it by the imposed symmetry of the components.

As seen in FIG. 5, the emitter lens 32 and the receiver lens 35 have convex surfaces on the side pointing away from the drip chamber 13. Thus, they expose only their flat surfaces 54 and 71 toward the chamber 13. This allows for the facile insertion and removal of the chamber 13 in the holder 20 of FIG. 1 with less chance of scratching the lenses 32 and 35 by the chamber's movement.

The derivation of the actual equations used to construct the lenses 32 and 35 becomes significantly simplier when it makes use of the various symmetry and operational conditions imposed upon the system. Initially, of course, the system displays bilateral symmetry about both the midline 81 and the longitudinal midplane 82 as seen in FIG. 5. Taking the intersection of these two lines as the origin (0,0) of the x-y axes in the figure, the calculation of one quadrant by the substitutions of $-x$ for x or $-y$ for y permits the rapid determination of the appropriate results in the other three quadrants. Further, as discussed above, the radiation is collimated along the path segment P1 as it travels in air between the emitter reflector 30 and the emitter lens 32, along the path segment P5 in the interior of the drip chamber 13, and along the path segment P9 as it travels between the receiver lens 35 and the receiver reflector 36. Lastly, to avoid damage the face 54 of the emitter lens 32 and the face 71 of the receiver lens 35, posit a flat surface toward the drip chamber 13. This reduces the likelihood of their damage as the drip chamber 13 moves in and out of the detector 20 of FIG. 1. If they had convex surfaces, as seen on the opposing faces 52 and 73, the motion of the drip chamber could very well bring it into contact with the interior surfaces of these lenses and damage them.

As a result of the foregoing, the calculation of the light path, especially with regards to determining the rear surface 73 of the lens 35, will take place for the upper right quadrant of the diagram seen in FIG. 5. The rear lens surface 73 represents the only undetermined optical component of the system.

Additionally, the actual calculations require the actual knowledge of the indices of refraction for both the drip chamber 13 and the lenses 32 and 36. This requires some care not merely to use the published index of refraction for the material. The index actually constitutes a function of the wavelength of radiation used. Thus, the index should be actually determined experimentally for the particular radiation employed for the measurements. The drip chamber 13 often has a composition of a vinyl whereas the lenses 32 and 35 have a composition of an acrylic. Furthermore, the placement of the flat surface 71 of the lens 35 consitutes a matter of choice. This in effect determines $y_3$. Moreover, the thickness of the lens 35 should at least suffice to accommodate the convex surface 73 on its rear side. Other than that, the actual thickness represents a matter of choice. Thus, for example, a thickness of 0.140 inch along the axis $x=0$ allows the remaining calculations to proceed.

Figure 6:
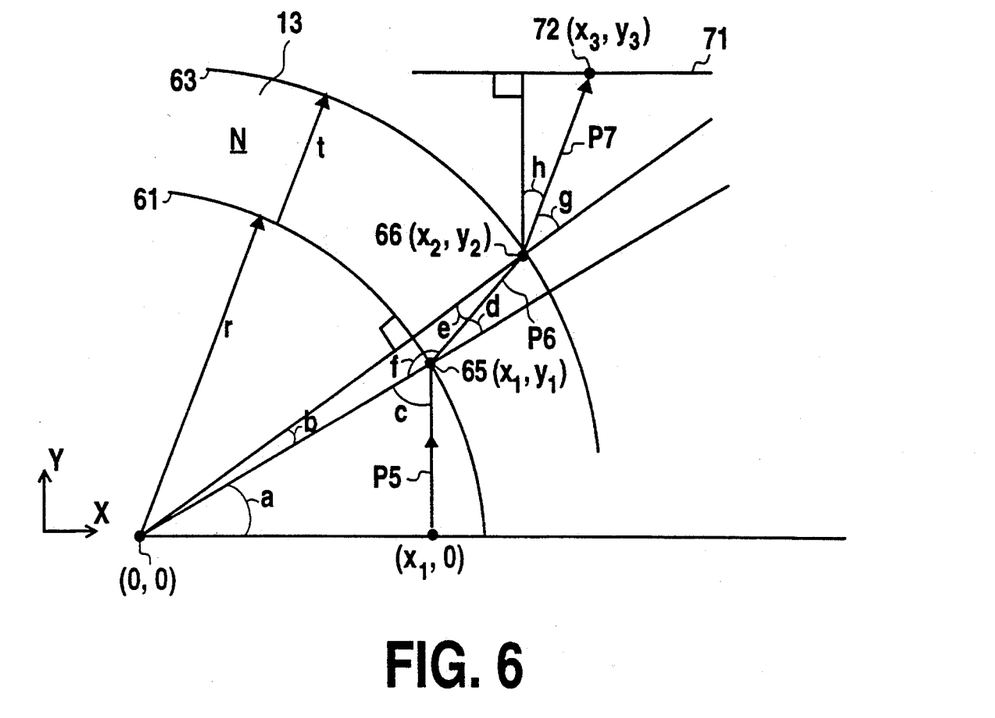
FIG. 6 diagrams the analysis of the light path through the wall of the drip chamber.
Figure 7:
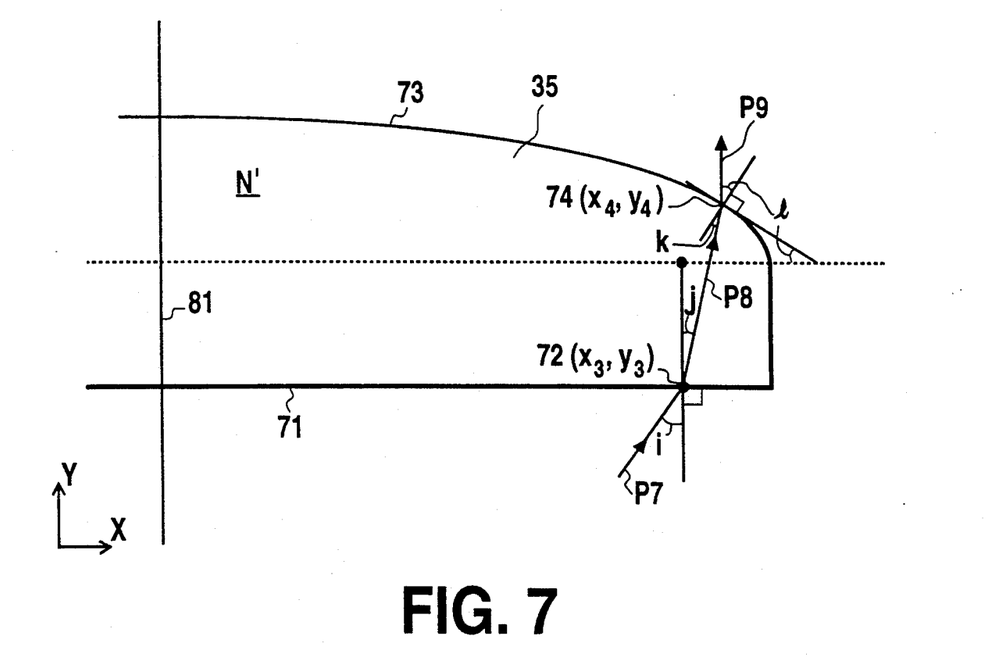
FIG. 7 provides a diagram for the analysis of the light path taken through the optical components after it has passed through the drip chamber.

The calculation commences with the light crossing the $y=0$ axis at $x=x_1$ as seen in FIG. 6. Thus, it starts with the path segment P5 as it crosses the $y=0$ axis at the point $(x_1, 0)$ as shown in FIG. 6. It will strike the interior surface 61 of the drip chamber 13 at the point 65 which has the coordinates of $(x_2, y_2)$. The procedure then involves moving $x_1$ over to the right by a specified increment, in this case 0.005 inch, and carrying out the appropriate calculations for this particular $x_1$. This results in the equations (1) through (6) below.

$$d = \sin^{-1}((1/N)\sin c) \tag{1}$$

$$e = \sin^{-1}((r/r+t)\sin f) \tag{2}$$

$$g = \sin^{-1}(N \sin e) \tag{3}$$

$$x_3 = (y_3 - y_2)\tan h + x_2 \tag{4}$$

$$j = \sin^{-1}((1/N')\sin i) \tag{5}$$

$$O = \sin^{-1}((1/N')\sin l) - l + j \tag{6}$$

Equations (1) and (3) above make use of the usual Snell's law for the change in direction of a light beam at an interface between two materials having different indices of refraction. Of course, air has an index of refraction very close to one. The index of refraction for the chamber 13 is represented by N and that for the lens 35 by N'.

Equation (6) does not permit a direct calculation since it includes terms for both (sin l) and l itself. Accordingly, it requires a numerical solution. Upon its completion, the calculation may then proceed to equation 7:

$$x_4 = x_3 + (py_4 - y_3) \sin j \quad (7)$$

Figure 8:
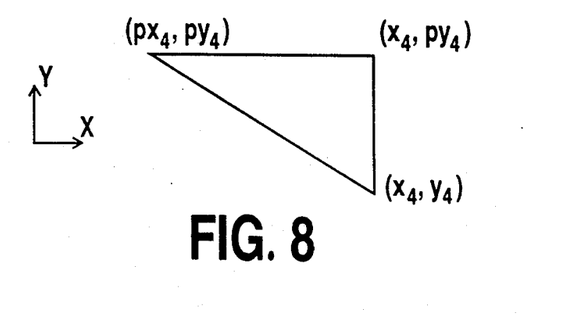
FIG. 8 shows the basis for the iterative procedure for determining the shape of the optics in the light path of the components as shown in FIGS. 1 through 4 and FIG. 7.

Presumably, equation 7 might be considered to have two unknowns, $x_4$ and "$py_4$". However, as shown in FIG. 8, the calculation does not directly calculate $x_4$ and $y_4$ simultaneously. Rather, it calculates $x_4$ by assuming that the old, previous $y_4$, labeled as "$py_4$" is valid for the new $x_4$. This thus gives the point in the upper right hand corner of the triangle in FIG. 8. Naturally, it involves the approximation that the $x_4$ calculated using the previous $y_4$ (i.e., "$py_4$") is sufficiently close for all nominal purposes. In fact, this assumption proves entirely correct especially in light of the fact that the steps taken across the drip chamber 13 in moving from one $x_1$ to another $x_1$ amounts to only 0.005 inch. As a further note, equation 7 uses "sin j". More technically, it should use "tan j". However, for the small angles involved, the tangent and the sine very closely approximate each other.

With the calculation of the point ($x_4$, $py_4$), all that remains is the determination of the point ($x_4$, $y_4$) which lies in the lower right hand corner of the triangle in FIG. 8. This proceeds through equation 8 which completes the calculation for a particular $x_1$.

$$y_4 = py_4 - ((x_4 - px_4) \tan l) \quad (8)$$

The calculations continue until the stepping of $x_1$ across the drip chamber 13 reaches its inner surface 61. This permits the construction of the rear surface 73 of the receiver lens 35.

Accordingly, what is claimed is:
1. In a drop detector comprising:
   (1) emitter means for providing em. radiation;
   (2) receiver means for, upon the receipt of said em. radiation, providing a characteristic electrical signal;
   (3) retaining means, coupled to said emitter means and said receiver means, for holding a drip chamber composed of a material with a specified index of refraction and general shape through which drops of a liquid pass; and
   (4) optical means, coupled to said retaining means, for altering the path of said em. radiation from said emitter means through a particular drip chamber held by said retaining means and to said receiver means,
the improvement wherein said optical means places the em. radiation from said emitter means, prior to its entry into said particular chamber, in a direction that will result in the em. radiation being collimated when traveling in the interior of said particular chamber.

2. The improvement of claim 1 wherein (1) said emitter means provides the em. radiation from a first single location; (2) said receiver means receives said em. radiation at a second single location; (3) said optical means, prior to said em. radiation entering said particular chamber, expands the beam of said em. radiation from said first location to a width at least equal to about the interior dimension of said chamber, and after said em. radiation has exited said chamber, condenses the beam of said em. radiation from a width at least about equal to said interior dimension to said second location.

3. The improvement of claim 2 wherein said beam of said em. radiation, as it travels through the interior of said particular chamber, is substantially uniform within said interior.

4. The improvement of claim 3 wherein said optical means includes a first portion disposed is said path of said em. radiation between said emitter means and said particular chamber and a second portion disposed in said path of said em. radiation between said particular chamber and said receiver means and wherein said first portion and said second portion each present a substantially flat surface towards said particular chamber.

5. The improvement of claim 3 wherein said optical means, after said em. radiation has passed through said particular chamber, collimates said em. radiation.

6. The improvement of claim 5 wherein said optical means, prior to said em. radiation entering said particular chamber, collimates said em. radiation.

7. The improvement of claim 6 wherein said particular chamber has cylindrical symmetry about an axis lying perpendicular to the path of said beam through said chamber.

8. The improvement of claim 7 wherein said beam of said em. radiation, when said axis lies at an angle of up to about 30 degrees from said path, consititues at least a surface of a width covering substantially all of said interior dimension of said said chamber.

9. The improvement of claim 7 wherein said optical means bends said beam at least about 90 degrees between said emitter means and said particular chamber and further bends the beam at least about 90 degrees between said chamber and said receiver means.

10. The improvement of claim 9 wherein said optical means alters the path of said em. radiation passing through said particular chamber in a fashion that said path is symmetric about a plane passing through the center of said particular chamber and lying perpendicular to said path.

11. The improvement of claim 9 wherein said optical means achieves said bends of at least about 90 degrees through total internal reflectance.

12. The improvement of claim 9 wherein said optical means includes a first portion located between said emitter means and said particular chamber and a second portion located between said particular chamber and said receiver means and wherein the components of said first portion are identical to the components of said second portion.

13. The improvement of claim 9 wherein said emitter means provides infrared em. radiation and said receiver means provides said characteristic electrical signal upon the receipt of said infrared em. radiation.

14. In a drop detector comprising:
   (1) emitter means for providing em. radiation;
   (2) receiver means for, upon the receipt of said across em. radiation, providing a characteristic electrical signal;
   (3) retaining means, coupled to said emitter means and said receiver means, for holding a drip chamber composed of a material with a specified index of refraction and general shape through which drops of a liquid pass; and (4) optical means, coupled to said retaining means, having a first portion for altering the path of said em. radiation from said emitter through a particular drip chamber held by said retaining means and a second portion for altering the path of said em. radiation from said particular chamber to said receiver means, the improvement wherein said optical means, after said em. radiation has passed through said particular chamber and reached said second portion of said optical means, collimates said em. radiation.

15. The improvement of claim 14 wherein (1) said emitter means provides the em. radiation from a single location; (2) said receiver means receives said em. radiation at a second single location; (3) said optical means, prior to said em. radiation entering said particular chamber, expands the beam of said em. radiation from said first location to a width at least equal to about the interior dimension of said chamber, and after said em. radiation has exited said chamber, condenses the beam of said em. radiation from a width at least about equal to said interior dimension to said second location.

16. The improvement of claim 15 wherein said beam of said em. radiation, as it travels through the interior of said particular chamber, is substantially uniform within said interior.

17. The improvement of claim 16 wherein said optical means includes a first portion disposed is said path of said em. radiation between said emitter means and said particular chamber and a second portion disposed in said path of said em. radiation between said particular chamber and said receiver means and wherein said first portion and said second portion each present a substantially flat surface towards said particular chamber.

18. The improvement of claim 16 wherein said first portion of said optical means, prior to said em. radiation departing said first portion of said optical means, collimates said em. radiation.

19. The improvement of claim 18 wherein said particular chamber has cylindrical symmetry about an axis lying perpendicular to the path of said beam through said chamber.

20. The improvement of claim 19 wherein said beam of said em. radiation, when said axis lies at an angle of up to about 30 degrees from said path, consititues at least a surface of a width covering substantially all of said interior dimension of said said chamber.

21. The improvement of claim 19 wherein said optical means bends said beam at least about 90 degrees between said emitter means and said particular chamber and further bends the beam at least about 90 degrees between said chamber and said receiver means.

22. The improvement of claim 21 wherein said optical means alters the path of said em. radiation passing through said particular chamber in a fashion that said path is symmetric about a plane passing through the center of said particular chamber and lying perpendicular to said path.

23. The improvement of claim 21 wherein said optical means achieves said bends of at least about 90 degrees through total internal reflectance.

24. The improvement of claim 21 wherein said optical means includes a first portion located between said emitter means and said particular chamber and said second portion located between said particular chamber and said receiver means and wherein the components of said first portion are identical to the components of said second portion.

25. The improvement of claim 21 wherein said emitter means provides infrared em. radiation and said receiver means provides said characteristic electrical signal upon the receipt of said infrared em. radiation.

26. In a drop detector comprising:
(1) emitter means for providing em. radiation;
(2) receiver means for, upon the receipt of said em. radiation, providing a characteristic electrical signal;
(3) retaining means, coupled to said emitter means and said receiver means, for holding a drip chamber composed of a material with a specified index of refraction and general shape through drops of a liquid pass; and
(4) optical means, coupled to said retaining means, for, altering the path of said em. radiation from said emitter through a particular drip chamber held by said retaining means and to said receiver means, the improvement wherein said optical means alters the path of said em. radiation passing through said particular chamber in a fashion that said path is symmetric about a plane passing through the center of said particular chamber and lying perpendicular to said path.

27. The improvement of claim 26 wherein (1) said emitter means provides the em. radiation from a first single location; (2) said receiver means receives said em. radiation at a second single location; (3) said optical means, prior to said em. radiation entering said particular chamber, expands the beam of said em. radiation from said first location to a width at least equal to about the interior dimension of said chamber, and after said em. radiation has exited said chamber, condenses the beam of said em. radiation from a width at least about equal to said interior dimension to said second location.

28. The improvement of claim 27 wherein said beam of said em. radiation, as it travels through the interior of said particular chamber, is substantially uniform within said interior.

29. The improvement of claim 28 wherein said optical means includes a first portion disposed is said path of said em. radiation between said emitter means and said particular chamber and a second portion disposed in said path of said em. radiation between said particular chamber and said receiver means and wherein said first portion and said second portion each present a substantially flat surface towards said particular chamber.

30. The improvement of claim 28 wherein said particular chamber has cylindrical symmetry about an axis lying perpendicular to the path of said beam through said chamber.

31. The improvement of claim 30 wherein said beam of said em. radiation, when said axis lies at an angle of up to about 30 degrees from said path, consititues at least a surface of a width covering substantially all of said interior dimension of said said chamber.

32. The improvement of claim 30 wherein said optical means bends said beam at least about 90 degrees between said emitter means and said particular chamber and further bends the beam at least about 90 degrees between said chamber and said receiver means.

33. The improvement of claim 32 wherein said optical means achieves said bends of at least about 90 degrees through total internal reflectance.

34. The improvement of claim 32 wherein said optical means includes a first portion located between said emitter means and said particular chamber and a second portion located between said particular chamber and said receiver means and wherein the components of said first portion are identical to the components of said second portion.

35. The improvement of claim 32 wherein said emitter means provides infrared em. radiation and said receiver means provides said characteristic electrical signal upon the receipt of said infrared em. radiation.

36. In a drop detector comprising:
   (1) emitter means for providing em. radiation from a first single location;
   (2) receiver means for, upon the receipt of said em. radiation at a second single location, providing a characteristic electrical signal;
   (3) retaining means, coupled to said emitter means and said receiver means, for holding a drip chamber composed of a material with a specified index of refraction and general shape through which drops of a liquid pass; and
   (4) optical means, coupled to said retaining means, for altering the path of said em. radiation from said emitter through a particular drip chamber held by said retaining means and to said receiver means,
the improvement wherein said optical means, prior to said em. radiation entering said particular chamber, expands the beam of said em. radiation from said first location to a width at least about equal to the interior dimension of said chamber, makes said beam substantially uniform within said interior of said particular chamber as it travels through said interior of said particular chamber, and after said em. radiation has exited said chamber, condenses a beam of said em. radiation of a width at least about equal to said interior dimension to said second location.

37. The improvement of claim 36 wherein said particular chamber has cylindrical symmetry about an axis lying perpendicular to the path of said beam through said chamber.

38. The improvement of claim 37 wherein said beam of said em. radiation, when said axis lies at an angle of up to about 30 degrees from said path, consititues at least a surface of a width covering substantially all of said interior dimension of said said chamber.

39. The improvement of claim 37 wherein said optical means includes a first portion disposed is said path of said em. radiation between said emitter means and said particular chamber and a second portion disposed in said path of said em. radiation between said particular chamber and said receiver means and wherein said first portion and said second portion each present a substantially flat surface towards said particular chamber.

40. The improvement of claim 37 wherein said optical means bends said beam at least about 90 degrees between said emitter means and said particular chamber and further bends the beam at least about 90 degrees between said chamber and said receiver means.

41. The improvement of claim 40 wherein said optical means achieves said bends of at least about 90 degrees through total internal reflectance.

42. The improvement of claim 40 wherein said emitter means provides infrared em. radiation and said receiver means provides said characteristic electrical signal upon the receipt of said infrared em. radiation.

43. The improvement of claim 40 wherein said optical means includes a first portion located between said emitter means and said particular chamber and a second portion located between said particular chamber and said receiver means and wherein the components of said first portion are identical to the components of said second portion.

44. In a method of detecting drops through a drip chamber located in an area including:
   (1) passing em. radiation through said chamber in said area;
   (2) receiving at least a portion of said em. radiation after is gas been passed through said area; and
   (3) determining the magnitude of said portion of said em. radiation,
the improvement comprising placing said em. radiation, prior to its passage through said chamber, in a direction that will result in said radiation being collimated as it travels in the interior of said chamber.

45. The improvement of claim 44 wherein (a) said em. radiation passes through said chamber emanates from a first single location; (b) the portion of said em. radiation received after it has passed through said area is received at a second single location; and (c) prior to said em. radiation entering said chamber, the beam of said radiation is expanded to a width at least equal to the interior dimension of said chamber and after said beam has exited said chamber, said beam of a width at least about equal to said interior dimension is condensed to said second location.

46. The improvement of claim 45 wherein said em. radiation, as it passes through said chamber, is substantially uniform across said chamber.

47. The improvement of claim 46 further comprising collimating said said em. radiation after said radiation has passed through said chamber.

48. The improvement of claim 47 further comprising collimating said em. radiation before said radiation has entered said chamber.

49. The improvement of claim 48 wherein said chamber has substantial cylindrical symmetry.

50. The improvement of claim 49 wherein said beam of said em. radiation, when the axis of said cylindrical symmetry lies at an angle of up to about 30 degrees from said path, consititues at least a surface of a width covering substantially all of said interior dimension of said said chamber.

51. In a method of detecting drops through a drip chamber located in an area including:
   (1) passing em. radiation through said chamber in said area;
   (2) receiving at least a portion of said em. radiation after it has passed through said area; and
   (3) determining the magnitude of said portion of said em. radiation,
the improvement comprising collimating said em. radiation after said radiation has passed through said chamber.

52. The improvement of claim 51 wherein (a) said em. radiation passed through said chamber emanates from a first single location; (b) the portion of said em. radiation received after it has passed through said area is received at a second single location; and (c) prior to said em. radiation entering said chamber, the beam of said radiation is expanded to a width at least equal to the interior dimension of said chamber and after said beam has exited said chamber, said beam of a width at least about equal to said interior dimension is condensed to said second location.

53. The improvement of claim 52 wherein said em. radiation, as it passes through said chamber, is substantially uniform across said chamber.

54. The improvement of claim 53 further comprising collimating said em. radiation before said radiation has entered said chamber.

55. The improvement of claim 54 wherein said chamber has substantial cylindrical symmetry.

56. The improvement of claim 55 wherein said beam of said em. radiation, when the axis of said cylindrical symmetry lies at an angle of up to about 30 degrees from said path, consititues at least a surface of a width covering substantially all of said interior dimension of said said chamber.

57. In a method of detecting drops through a drip chamber located in an area including:
(1) passing em. radiation through said chamber in said area;
(2) receiving at least a portion of said em. radiation after it has passed through said area; and
(3) determining the magnitude of said portion of said em. radiation, the improvement comprising altering the path of said em. radiation in a fashion that said path is symmetrical about a plane passing through the center of said chamber and lying perpendicular to said path.

58. The improvement of claim 57 wherein said em. radiation, as it passes through said chamber, is substantially uniform across said chamber.

59. The improvement of claim 49 further comprising collimating said em. radiation before said radiation has entered said chamber.

60. The improvement of claim 59 wherein said chamber has substantial cylindrical symmetry.

61. The improvement of claim 60 wherein said beam of said em. radiation, when the axis of said cylindrical symmetry lies at an angle of up to about 30 degrees from said path, consititues at least a surface of a width covering substantially all of said interior dimension of said chamber.

62. The improvement of claim 60 wherein (a) said em. radiation passed through said chamber emanates from a first single location; (b) the portion of said em. radiation received after it has passed through said area is received at a second single location; and (c) prior to said em. radiation entering said chamber, the beam of said radiation is expanded to a width at least equal to the interior dimension of said chamber and after said beam has exited said chamber, said beam of a width at least about equal to said interior dimension is condensed to said second location.

63. In a method of detecting drops through a drip chambered in an area including:
(1) passing through said chamber in said area em. radiation from a first single location;
(2) receiving at a second single location at least a portion of said em. radiation emanating from said first location; said
(3) determining the magnitude of said portion of said em. radiation, the improvement comprising (a), prior to said em. radiation entering said particular chamber, expanding the beam of said em. radiation from said first location to a width at least about equal to the interior dimension of said chamber, [and ] (b)making said beam substantially uniform as it travels through said interior of said chamber, and (c) after said beam has exited said chamber, condensing a beam of a width at least about equal to said interior dimension to said second location.

64. The improvement of claim 63 further comprising collimating said em. radiation before said radiation has entered said chamber.

65. The method of claim 64 wherein said chamber has substantial cylindrical symmetry.

66. The improvement of claim 65 wherein said beam of said em. radiation, when the axis of said cylindrical symmetry lies at an angle of up to about 30 degrees from said path, consititues at least a surface of a width covering substantially all of said interior dimension of said said chamber.

* * * * *